(12) United States Patent
Wittenberger

(10) Patent No.: US 8,672,930 B2
(45) Date of Patent: Mar. 18, 2014

(54) ENDOLUMINAL ABLATION CRYOBALLOON AND METHOD

(75) Inventor: Dan Wittenberger, L'ile Bizard (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 820 days.

(21) Appl. No.: 12/845,492

(22) Filed: Jul. 28, 2010

(65) Prior Publication Data

US 2012/0029495 A1 Feb. 2, 2012

(51) Int. Cl.
*A61B 18/02* (2006.01)

(52) U.S. Cl.
USPC .............................................. 606/21; 606/27

(58) Field of Classification Search
USPC .................................. 606/20–31, 41, 48–50
See application file for complete search history.

(56) References Cited

U.S. PATENT DOCUMENTS

| | | | |
|---|---|---|---|
| 5,486,192 A | 1/1996 | Walinsky et al. | |
| 6,283,959 B1 | 9/2001 | Lalonde et al. | |
| 6,758,830 B1 | 7/2004 | Schaer et al. | |
| 6,817,999 B2 | 11/2004 | Berube et al. | |
| 7,374,553 B2 | 5/2008 | Koerner et al. | |
| 7,442,190 B2 * | 10/2008 | Abboud et al. | 606/21 |
| 7,527,622 B2 * | 5/2009 | Lane et al. | 606/21 |
| 2001/0007070 A1 | 7/2001 | Stewart et al. | |
| 2005/0171527 A1 | 8/2005 | Bhola | |
| 2006/0106375 A1 | 5/2006 | Werneth et al. | |
| 2007/0032783 A1 * | 2/2007 | Abboud et al. | 606/21 |
| 2008/0171976 A1 | 7/2008 | Rios et al. | |
| 2009/0287203 A1 | 11/2009 | Mazzone et al. | |
| 2012/0029496 A1 * | 2/2012 | Smith | 606/21 |
| 2012/0065554 A1 * | 3/2012 | Pikus | 601/2 |
| 2012/0089047 A1 * | 4/2012 | Ryba et al. | 600/554 |

FOREIGN PATENT DOCUMENTS

WO 2008077082 A1 6/2008

* cited by examiner

*Primary Examiner* — Michael Peffley
(74) *Attorney, Agent, or Firm* — Christopher & Weisberg, P.A.

(57) ABSTRACT

A method of ablating tissue is provided, including positioning an expandable element of a catheter in a blood vessel; inflating the expandable element with a volume of refrigerant to substantially occlude the blood vessel; measuring the volume of refrigerant used to inflate the expandable element; correlating the measured volume to an inflated dimension of the expandable element; defining at least one of a target pressure within the expandable element and a target flow rate for refrigerant delivery to the expandable element based at least in part on the inflated dimension; regulating refrigerant delivery to the expandable element to attain the at least one defined target pressure within the expandable element or defined target flow rate for fluid delivery to the expandable element; and ablating at least a portion of the blood vessel with the expandable element.

17 Claims, 5 Drawing Sheets

ENDOLUMINAL ABLATION CRYOBALLOON AND METHOD

CROSS-REFERENCE TO RELATED APPLICATION

N/A

STATEMENT REGARDING FEDERALLY SPONSORED RESEARCH OR DEVELOPMENT

N/A

FIELD OF THE INVENTION

The present invention relates to medical devices and methods of use thereof for thermally treating tissue, and more specifically to a method and system for controlling the operation of balloon catheters in order to safely and effectively treat a tissue region.

BACKGROUND OF THE INVENTION

Numerous procedures involving catheters and other minimally invasive devices may be performed to provide a wide variety of treatments, such as ablation, angioplasty, dilation or the like. Such procedures often include positioning minimally-invasive devices, such as balloon catheters, within varying physiological locations throughout the body, including vascular regions such as arteries, veins, or other blood vessels. Vascular-based diagnoses and treatments can introduce challenges to the effective positing and operation of an inserted medical device or instrument. For example, a device or instrument may need to be routed through a blood vessel to a target location in the midst of normal (if not turbulent or disturbed) blood flow through the vessel, which results in varying thermal loads on the device being used. For thermally-based procedures, such as tissue ablation, the unpredictable, often-changing thermal load presented by such an environment can greatly alter the efficacy of a device and its ability to deliver the desired therapy in a given time period.

In addition to the varying, thermally-loaded surroundings, blood vessels and endoluminal tissues can have widely varying dimensions from one patient to the next. As a result, a device appropriately sized for a particular application or procedure in one patient may not be suitable for a similar application in someone having smaller stature or tissue structure. For example, when a balloon catheter is employed, it is often manufactured or constructed having particular shape or dimension for a specific application, and as such, any given catheter with a balloon may be limited to use in situations where the fixed dimensions of the balloon are appropriate. As such, the availability of multiple catheters having varying fixed dimensions may be needed to successfully perform a series of desired treatments.

In view of the above, it would be desirable to provide a medical device having an expandable element, such as a balloon, in which the particular size, shape, and/or dimensions of the balloon may be controlled and modified during use, and it would be further desirable to control the operation of a such a device to account for varying environmental conditions in the vicinity of the device in order to safely and effectively treat a tissue region.

SUMMARY OF THE INVENTION

The present invention advantageously provides a system having an expandable element, such as a balloon, in which the particular size, shape, and/or dimensions of the balloon may be controlled and modified during use, and which may further provide for controlling the operation of a such a device to account for varying environmental conditions in the vicinity of the device in order to safely and effectively treat a tissue region.

In particular, a method of treating tissue is provided, including positioning an expandable element of a medical device in a blood vessel, such as a renal artery; delivering a fluid to the expandable element such that the expandable element is inflated to substantially occlude the blood vessel; measuring an amount of fluid delivered to the expandable element; defining at least one of a target pressure within the expandable element, target temperature of the expandable element, and target flow rate for fluid delivery to the expandable element based at least in part on the measured volume; regulating fluid delivery to the expandable element to attain the at least one defined target pressure, defined target temperature, or defined target flow rate; and thermally affecting the blood vessel with the expandable element. The method may include correlating the measured amount to an inflated dimension of the expandable element; and assessing the occlusion of the blood vessel by measuring a pressure in the blood vessel, measuring a flow rate in the blood vessel, or measuring an impedance with the medical device. The method may also include monitoring a heart rate and modifying fluid delivery to the expandable element based at least in part on the heart rate. In addition, thermally affecting the blood vessel with the expandable element may include ablating a portion of the blood vessel and/or ablating nerve tissue in proximity to the blood vessel. The method may also include terminating fluid delivery to the expandable element; and controllably evacuating fluid from the expandable element such that the expandable element remains substantially inflated until the expandable element achieves a predetermined temperature.

A method of ablating tissue is also provided, including positioning an expandable element of a catheter in a blood vessel; inflating the expandable element with a volume of refrigerant to substantially occlude the blood vessel; measuring the volume of refrigerant used to inflate the expandable element; correlating the measured volume to an inflated dimension of the expandable element; defining at least one of a target pressure within the expandable element and a target flow rate for refrigerant delivery to the expandable element based at least in part on the inflated dimension; regulating refrigerant delivery to the expandable element to attain the at least one defined target pressure within the expandable element or defined target flow rate for fluid delivery to the expandable element; and ablating at least a portion of the blood vessel with the expandable element. The method may also include measuring a pressure within the expandable element, and modifying refrigerant delivery based at least in part on the measured pressure; and/or measuring a flow rate of refrigerant being delivered to the expandable element, and modifying refrigerant delivery based at least in part on the measured flow rate.

In another aspect, a method of ablating tissue is provided, including positioning an expandable element of a catheter in a blood vessel; inflating the expandable element with a volume of refrigerant to substantially occlude the blood vessel; measuring the volume of refrigerant used to inflate the expandable element; correlating the measured volume to an inflated dimension of the expandable element; defining at least one of a target pressure within the expandable element and a target flow rate for refrigerant delivery to the expandable element based at least in part on the inflated dimension;

measuring at least one of a pressure within the expandable element and a flow rate of refrigerant being delivered to the expandable element; regulating refrigerant delivery to the expandable element based at least in part on the measured pressure or measured flow rate to attain the at least one defined target pressure or defined target flow rate; and ablating at least a portion of the blood vessel with the expandable element.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
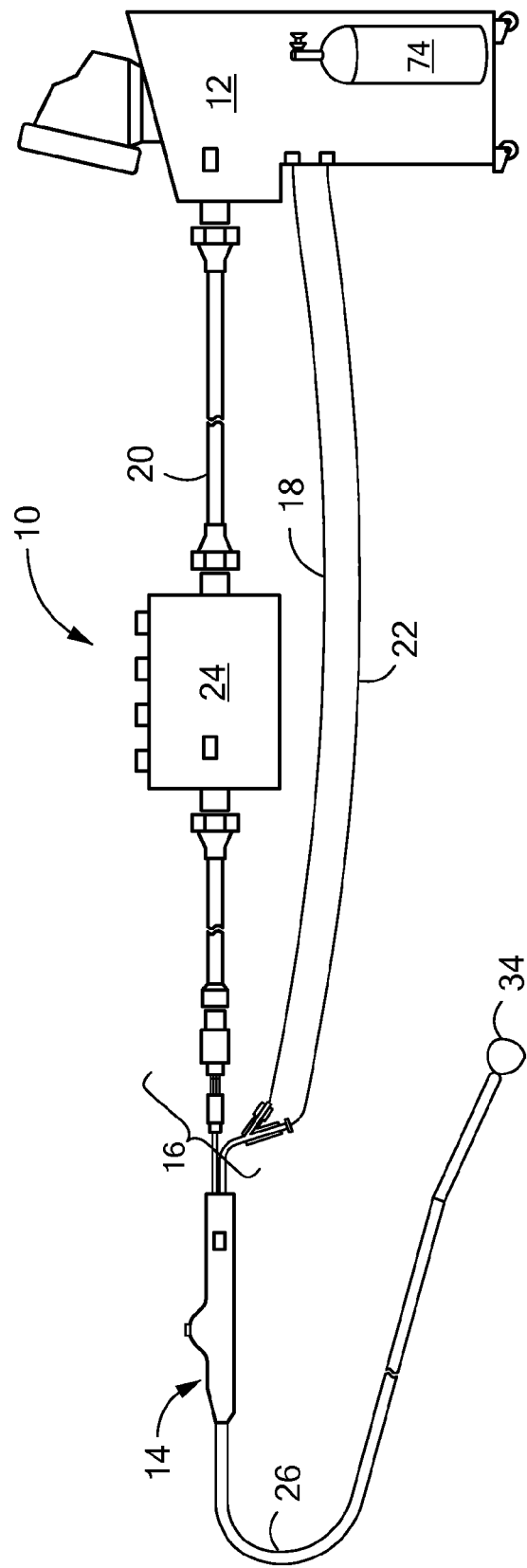
FIG. 1 is an illustration of an embodiment of a medical system constructed in accordance with the principles of the present invention.

The present invention advantageously provides a system having an expandable element, such as a balloon, in which the particular size, shape, and/or dimensions of the balloon may be controlled and modified during use, and which may further provide for controlling the operation of a such a device to account for varying environmental conditions in the vicinity of the device in order to safely and effectively treat a tissue region. Referring now to the drawing figures in which like reference designations refer to like elements, an embodiment of a medical system constructed in accordance with principles of the present invention is shown in FIG. 1 and generally designated as "10." The system generally includes a cooling unit or console 12 coupled to a medical device 14 through an umbilical system 16. The medical device 14 may be a medical probe, a catheter, a balloon-catheter, as well as other devices deliverable or otherwise positionable through the vasculature and/or proximate to a tissue region for treatment. In particular, the medical device 14 may include a device operable to thermally treat a selected tissue site, including blood vessels and adjacent structures, cardiac or renal tissue. The medical system 10 may also include one or more sensors to monitor the operating parameters throughout the system, including for example, pressure, temperature, flow rates, volume, or the like in the console 12, the umbilical system 16, and/or the medical device 14.

Umbilical system 16 may include three separate umbilicals: a coaxial umbilical 18, an electrical umbilical 20 and a vacuum umbilical 22. Although separate umbilicals are shown, it is contemplated that one or more connections may be included in one or more umbilicals having one or more coaxial or otherwise integrally contained passages or conduits therethrough providing electrical and fluid communication between the medical device 14 and the console 12. An outer vacuum umbilical may be suitable for a medical device having multiple layers or balloons. If the user wishes to perform a radiofrequency ("RF") ablation procedure, radiofrequency energy can be provided to electrodes on the medical device 14 via electrical umbilical 20 to perform an RF ablation technique. Electrical umbilical 20 can include an electrocardiograph ("ECG") box 24 to facilitate a connection from one or more electrodes on the medical device 14 to an ECG monitor (not shown). Coaxial umbilical 18 may include both a cooling injection umbilical and a vacuum umbilical that provide respective inlet and return paths for a refrigerant or coolant used to cool a tissue-treating section of the device 14. The vacuum umbilical 22 may provide a safety conduit allowing excess coolant or gas to escape from the device 14 if the pressure within the medical device 14 exceeds a predefined limit. The vacuum umbilical 22 can also be used to capture air through a leak of the outer vacuum system where it is outside the patient and as a lumen to ingress blood when inside the patient.

Figure 2:
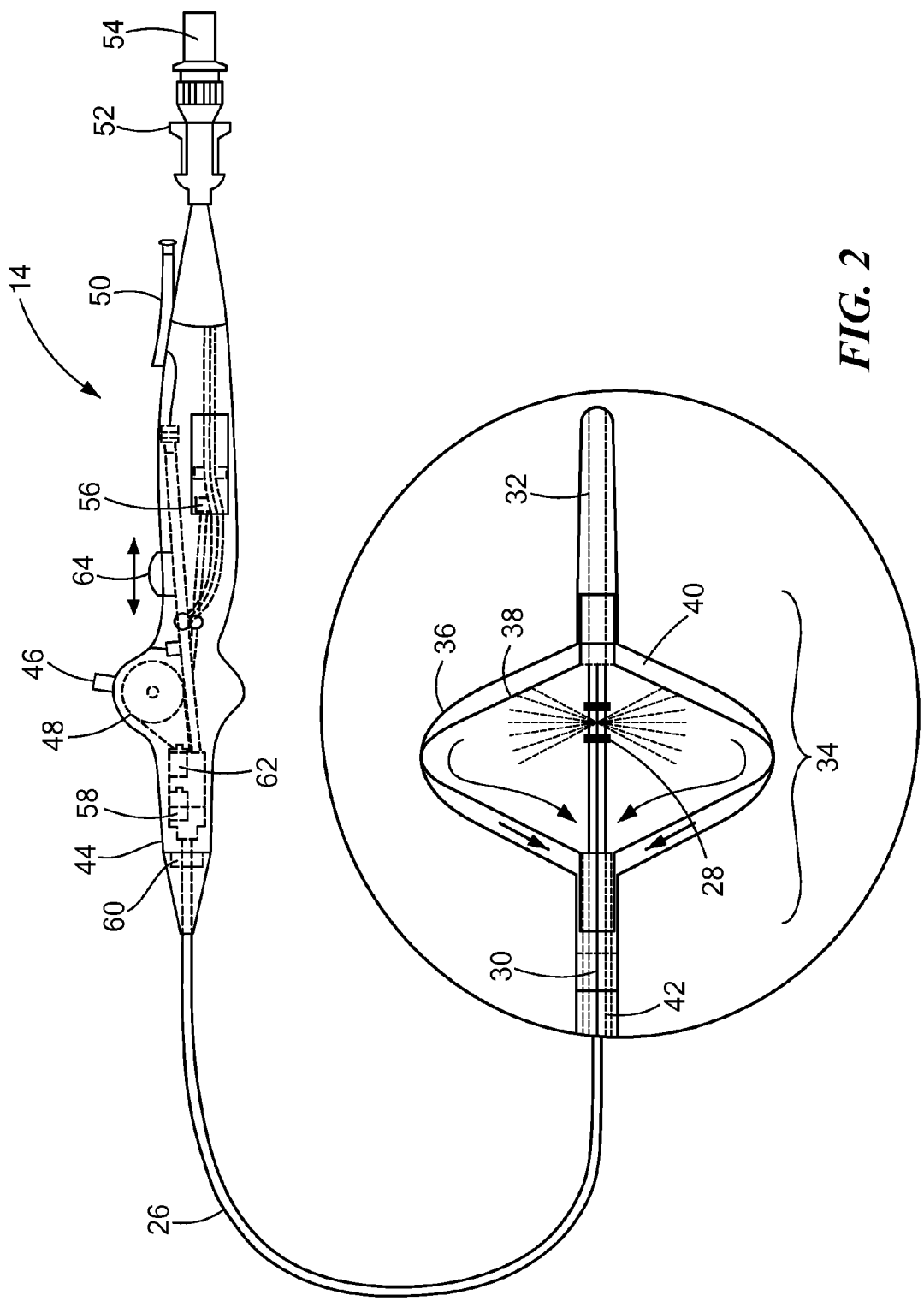
FIG. 2 is an illustration of an embodiment of a medical device for use with the system shown in FIG. 1.

Now referring to FIG. 2, the medical device 14 is shown in more detail. The medical device 10 may include an elongate body 26 passable through a patient's vasculature. The elongate body 26 may define a proximal portion and a distal portion, and may further include one or more lumens may disposed within the elongate body 26 thereby providing mechanical, electrical, and/or fluid communication between the proximal portion of the elongate body 26 and the distal portion of the elongate body 26. For example, the elongate body 26 may include an injection lumen 28 and an exhaust lumen 30 defining a fluid flow path therethrough. In addition, the elongate body 26 may include a guide wire lumen 32 movably disposed within and/or extending along at least a portion of the length of the elongate body 26 for over-the-wire applications. The guide wire lumen 32 may define a proximal end and a distal end, and the guide wire lumen 32 may be movably disposed within the elongate body 26 such that the distal end of the guide wire lumen 32 extends beyond and out of the distal portion of the elongate body 26.

The medical device may include one or more treatment regions for energetic or other therapeutic interaction between the medical device 14 and a treatment site. The treatment regions may deliver, for example, radiofrequency energy, cryogenic therapy, or the like. For example, the device 14 may include a first treatment region 34 having a thermal treatment element, such as an expandable membrane or balloon and/or one or more electrodes or other thermally-transmissive components, at least partially disposed on the elongate catheter body. In a particular example, the first treatment region 34 may include a first expandable/inflatable element or balloon 36 defining a proximal end coupled to the distal portion of the elongate body 26 of the medical device 14, while further defining a distal end coupled to the distal end of the guide wire lumen 32. As such, due to the movable nature of the guide wire lumen 32 about the elongate body 26, any axial and/or longitudinal movement of the guide wire lumen 32 may act to tension or loosen the first expandable element 36, i.e., extend or retract the expandable element 36 from a lengthened state to a shortened state during an inflation or deflation thereof. In addition, the first expandable element 36 may have any of a myriad of shapes, and may further include one or more material layers providing for puncture resistance, radiopacity, or the like. The first expandable element 36 may be in communication with the fluid injection and exhaust lumens of the medical device 14 as described above.

The medical device 14 may further include a second expandable/inflatable element or balloon 38 contained within or otherwise encompassed by the first expandable element 36 such that an interstitial region, envelope or space 40 is defined therebetween. The second expandable element 38 may be in communication with the fluid injection and exhaust lumens of the medical device 14 as described above, i.e., a fluid flow path may provide an inflation fluid or coolant, such as a cryogenic fluid or the like, to the interior of the second expandable element 38. Further, the interstitial region 40 may be in fluid communication with an interstitial lumen 42 providing a fluid flow path or avenue separate and independent from a fluid flow path delivering fluid or otherwise in communication with an interior of the second expandable element 38. The second pathway provides an alternate exhaust route for fluid that may leak from the interior of the second expandable element 38 into the interstitial region 40 or fluid entering the medical device 14 from the exterior. In particular, the isolation of the interstitial lumen 42 from the interior of the second expandable element 38 provides an alternate route for fluid to circulate in the case of a rupture or leak of either the first or second expandable elements, as well as allowing for the injection or circulation of fluids within the interstitial region 40 independently of fluids directed towards the second expandable element 38. Towards that end, the interstitial region may be in fluid communication with a fluid source, a vacuum source, or the like separate from a fluid source, vacuum source or otherwise in fluid communication with the interior of the second expandable element 38. Alternatively, the interstitial lumen 42 may be joined to or otherwise in fluid communication with the injection lumen 28 and the interior of the second expandable element 38 to provide a single exhaust or vacuum source for the medical device 14.

Continuing to refer to FIG. 2, the medical device 14 may include a handle 44 coupled to the proximal portion of the elongate body 26, where the handle 44 may include an element such as a lever or knob 46 for manipulating the catheter body and/or additional components of the medical device 14. For example, a pull wire 48 with a proximal end and a distal end may have its distal end anchored to the elongate body 26 at or near the distal end. The proximal end of the pull wire 48 may be anchored to an element such as a cam in communication with and responsive to the lever 46. The handle 44 can further include circuitry for identification and/or use in controlling of the medical device 14 or another component of the system.

Additionally, the handle may be provided with a fitting 50 for receiving a guidewire that may be passed into the guidewire lumen 32. The handle 44 may also include connectors that are matable directly to a fluid supply/exhaust and control unit or indirectly by way of one or more umbilicals. For example, the handle may be provided with a first connector 52 that is matable with the co-axial fluid umbilical 18 and a second connector 54 that is matable with the electrical umbilical 20. The handle 44 may further include blood detection circuitry 56 in fluid and/or optical communication with the injection, exhaust and/or interstitial lumens. The handle 44 may also include a pressure relief valve 58 in fluid communication with the injection, exhaust and/or interstitial lumens to automatically open under a predetermined threshold value in the event that value is exceeded.

The medical device 14 may further include one or more temperature, pressure, and/or flow sensors proximate or otherwise in communication with the treatment region(s) positioned for monitoring, recording and/or conveying measurements of conditions within the medical device 14 or the ambient environment at the distal portion of the medical device 14. The sensor(s) may be in communication with the console 12 for initiating or triggering one or more alerts or therapeutic delivery modifications during operation of the medical device 14. For example, the handle may include one or more pressure sensors 60 to monitor the fluid pressure within the lumens and/or treatment region of the medical device 14. The handle may also include one or more fluid flow rate sensors 62 to measure or record the fluid flow rate and/or an amount of fluid introduced into the lumens or treatment regions of the medical device 14 for any given time period. It is also contemplated that such sensors may be included or otherwise housed within the console 12 and its components, as described below.

Continuing to refer to FIG. 2, the medical device 14 may include an actuator element 64 that is movably coupled to the proximal portion of the elongate body 26 and/or the handle 44. The actuator element 64 may further be coupled to the proximal portion of the guide wire lumen 32 such that manipulating the actuator element 64 in a longitudinal direction causes the guide wire lumen 32 to slide towards either of the proximal or distal portions of the elongate body 26. As a portion of either and/or both the first and second expandable elements 36, 38 may be coupled to the guide wire lumen 32, manipulation of the actuator element 64 may further cause the expandable element(s) to be tensioned or loosened, depending on the direction of movement of the actuator element 64, and thus, the guide wire lumen 32. Accordingly, the actuator element 64 may be used to provide tension on the expandable element(s) 36, 38 during a particular duration of use of the medical device 14, such as during a deflation sequence, for example. The actuator element 64 may include a thumb-slide, a push-button, a rotating lever, or other mechanical structure for providing a movable coupling to the elongate body 26, the handle 44, and/or the guide wire lumen 32. Moreover, the actuator element 64 may be movably coupled to the handle 44 such that the actuator element 64 is movable into individual, distinct positions, and is able to be releasably secured in any one of the distinct positions.

In an exemplary system, a fluid supply or reservoir 66 including a coolant, cryogenic refrigerant, or the like, an exhaust or scavenging system (not shown) for recovering or venting expended fluid for re-use or disposal, as well as various control mechanisms for the medical system may be housed in the console 12. In addition to providing an exhaust function for the catheter fluid supply, the console 12 may also include pumps, valves, controllers or the like to recover and/or re-circulate fluid delivered to the handle 44, the elongate body 26, and treatment region 34 of the medical device 14. A vacuum pump in the console 12 may create a low-pressure environment in one or more conduits within the medical device 14 so that fluid is drawn into the conduit(s) of the elongate body 26, away from the treatment region 34, and towards the proximal end of the elongate body 26. The console 12 may include one or more controllers, processors, and/or software modules containing instructions or algorithms to provide for the automated operation and performance of the features, sequences, or procedures described herein.

Figure 3:
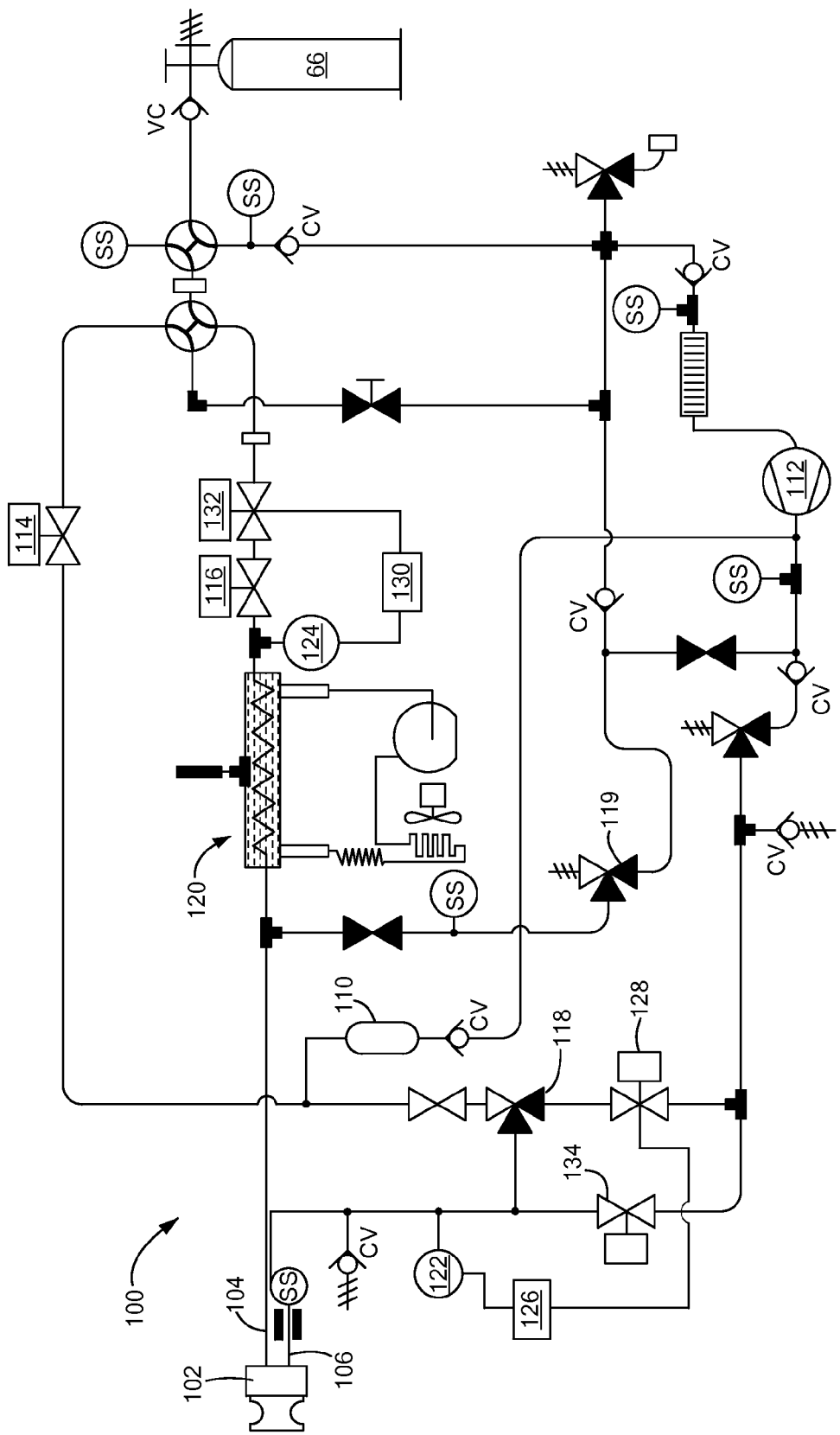
FIG. 3 is a schematic representation of an embodiment of a fluid delivery system of the medical system illustrated in FIG. 1.

Now referring to FIG. 3, a schematic representation of a fluid circulation system 100 of the console 12 for use with the medical device 14 is shown. As previously discussed, the console 12 includes various mechanical and/or electrical components (such as those illustrated for fluid circulation system 100) to assist in the operation, control, and/or monitoring of the medical device 14, described above. Primarily, the fluid circulation system 100 may be coupled to the medical device 14 through an umbilical connector 102, which places a supply lumen 104 and an exhaust lumen 106 of the fluid circulation system 100 in fluid communication with the respective lumens of the medical device 14. In general, the fluid circulation system 100 may further include the first fluid supply or reservoir 66, a second coolant reservoir 110, and a vacuum source 112. As used herein, the term 'reservoir' is intended to include any container or chamber able to contain a fluid. As such, either of the first or second reservoirs may include a tank, container, or even a length of tubing or the like defining an interior space between two or more valves. The second coolant reservoir 110 may have a volumetric capacity smaller than the volumetric capacity of the fluid supply 66 to reduce the likelihood of cardiac abnormalities and/or failure due to coolant egress into the vascular system and to contain a specific coolant amount for controlled release or circulation into the medical device 14. The vacuum source 112 may include any structure and/or apparatus able to provide a negative pressure gradient for providing fluid flow, including pumps, plunger devices, or the like.

One or more valves may be disposed about the fluid circulation system 100 in fluid communication with the supply lumen 104 and/or the exhaust lumen 106 for manipulating and/or providing fluid flow along a desired path. For example, the fluid circulation system 100 may include a pair of valves, 114 and 116, in fluid communication with the fluid supply 66 such that the fluid supply 66 may be selectively switched from being in fluid communication with the second coolant reservoir 110 to being in fluid communication with the supply lumen 104. Moreover, a valve 118 may be disposed on the exhaust lumen 106 such that the exhaust lumen 106 may be selectively switched from being in fluid communication with the second coolant reservoir 110 to being in fluid communication with the vacuum source 112. In addition, the fluid circulation system 100 may include one or more check valves and/or pressure relief valves CV configured to open to atmosphere or to a recovery tank should a pressure level and/or flow rate within a portion of the console 100 exceed a desired or predetermined level.

The fluid circulation system 100 may include a valve 119 in fluid communication with both the supply lumen 104 and the exhaust lumen 106. In particular, the valve 119 may be in fluid communication with the supply lumen 104 at a position upstream of the umbilical connector 102, while being in fluid communication with the exhaust lumen 106 downstream from the umbilical connector 102. The valve 119 may further be placed in fluid communication with the surrounding atmosphere to equalize pressure in both the exhaust and supply lumens. During operation, the fluid circulation system 100 and/or the console 12 may detect a failure of the medical device 14 (including, for example, the expandable element(s)), such as an indication of the presence of blood or bodily fluid being entrained into the coolant system. Upon such detection, coolant flow may be terminated. However, despite the termination of coolant flow, due to the built-up pressure levels in the supply and exhaust lumens, bodily fluid may continue to be siphoned into the medical device 14 and thus into portions of the fluid circulation system 100. To reduce the likelihood that siphoning occurs, the valve 119 may be actuated to place both the supply lumen 104 and the exhaust lumen 106 into fluid communication with the atmosphere. By doing so, the pressure in either lumen will be substantially equalized and thus will prevent the further ingress of bodily fluids into the medical device 14 and thus the console 12. Of course, the equalization and/or subjection of both the supply and exhaust lumens may be achieved by using one or more valves in various configuration.

The fluid circulation system 100 may also include a sub-cooler 120 disposed about a portion of the supply lumen 104 for achieving a desired temperature and/or coolant phase of fluid flowing therethrough. The subcooler 120 may include a compressor, condenser and the like placed in thermal communication with the supply lumen 104 as previously discussed.

One or more sensors may be disposed about the supply and exhaust lumens of the fluid circulation system 100 for detecting temperature, pressure, and/or flow rates through a particular portion of the fluid circulation system 100 and/or medical device 14. For example, a first pressure sensor 122 may be disposed about the exhaust lumen 106 proximate to the umbilical connector 102. In addition, a second pressure sensor 124 may be disposed about the supply lumen 104. Of course, additional sensors SS, which may include temperature, flow, or pressure sensors may be included throughout the fluid circulation system 100 for monitoring and/or controlling particular portions of the console and properties thereof. Exemplary locations for the sensors SS may include positions just upstream of the fluid supply 66, adjacent the connector 102, as well as upstream and downstream of the vacuum source 112, as illustrated in FIG. 3.

In addition to the one or more sensors, one or more controllers may be coupled to the sensors, and in turn, coupled to one or more of the valves situated throughout the fluid circulation system 100 such that the valves may be controllably manipulated in response to information obtained by the sensors. For example, a first controller 126 may be coupled to the first pressure sensor 122, wherein the first controller 126 is further coupled to a valve 128 disposed on a portion of the exhaust line, and where the valve 128 may also be in fluid communication with the vacuum source 112. In addition, a second controller 130 may be coupled to the second pressure sensor 124, where the second controller 130 is further coupled to a valve 132 disposed about the supply lumen 104. Accordingly, fluid flow through portions of the exhaust and/or supply lumens may be controllably manipulated in direct response to the information obtained by sensors contained therein.

Figure 4:
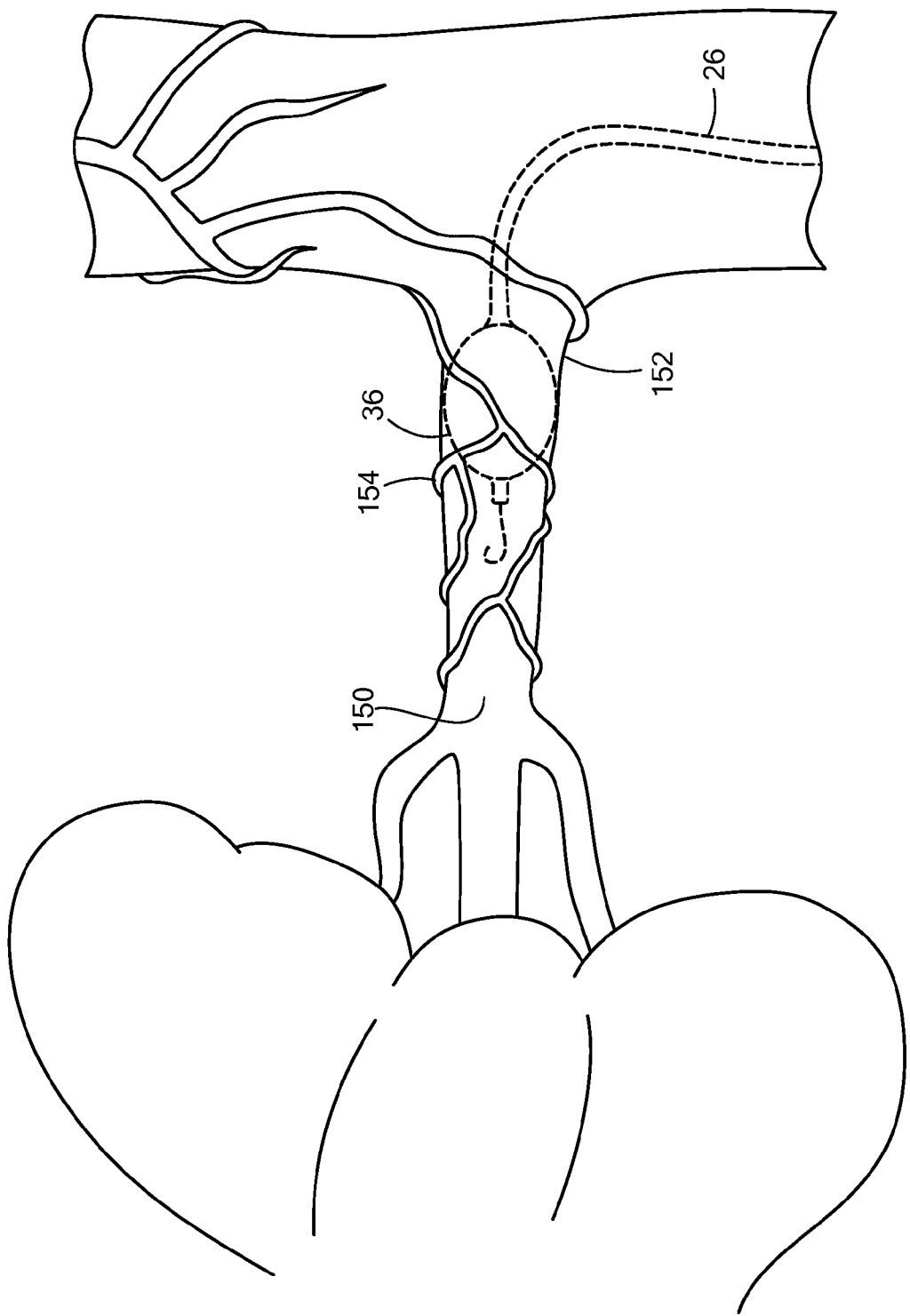
FIG. 4 an illustration of an exemplary use of a medical device constructed in accordance with the principles of the present invention.

Now referring to FIG. 4, in an exemplary method of use, the medical system 10 may be used to controllably deliver therapeutic treatment to a targeted tissue area. For example, the medical device 14 may be positioned and operated to ablate targeted tissue regions in the vasculature, such as a renal artery or the like. The first treatment region 34 may be positioned in an endoluminal passage 150 of a blood vessel, such as renal artery or vein. The expandable element of the treatment region 34 may be delivered or positioned in an unexpanded state in proximity to the tissue targeted for thermal ablation, which may include a portion of the vessel wall 152 defining the endoluminal passage, and tissue in proximity to or otherwise traversing portions of the endoluminal wall, including nerves 154. The fluid circulation system 100 of the console 12 may then be operated to controllably inflate and operate the treatment region 34 of the medical device 14 in response to one or measured parameters and their resulting effects within the targeted tissue area.

Figure 5:
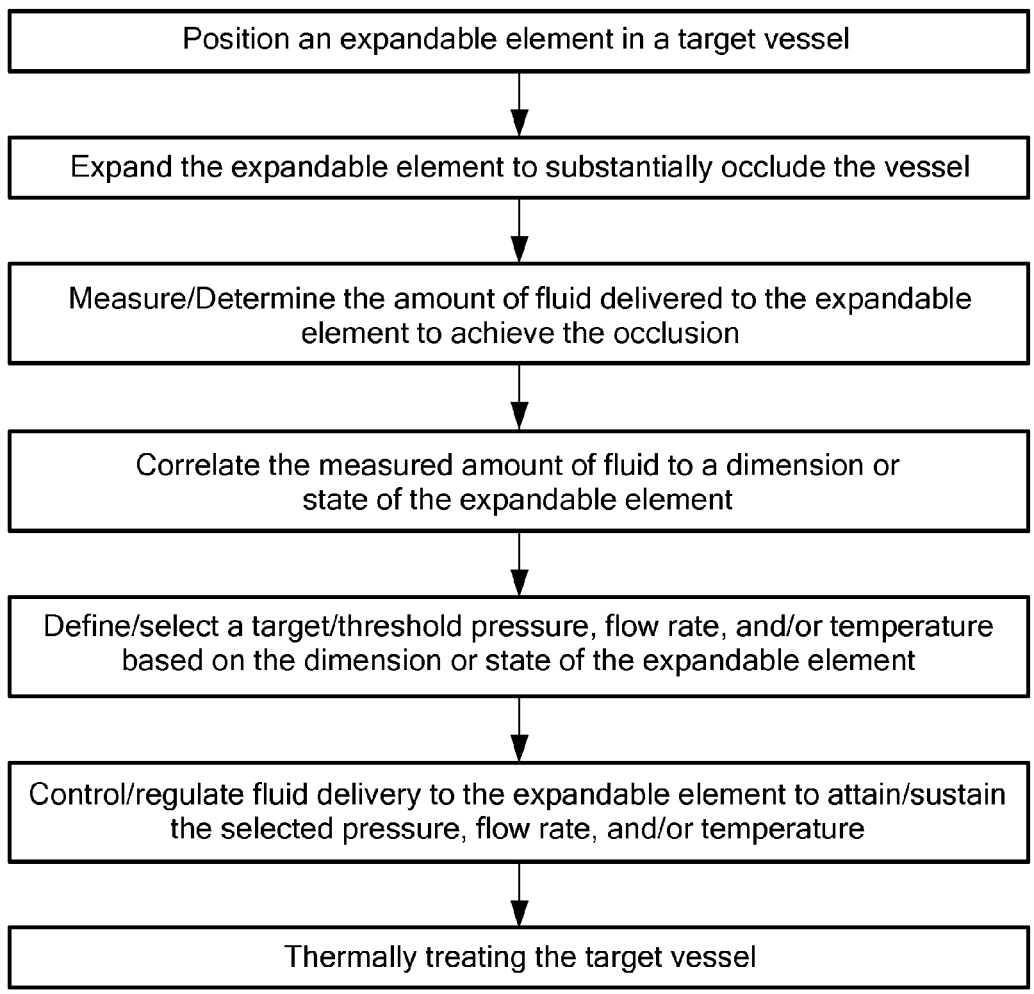
FIG. 5 is a flow chart of an exemplary use of the medical system of FIG. 1 in accordance with the present invention.

Now turning to FIG. 5, a flow chart of such an exemplary method of operation is provided. As mentioned above, the expandable elements 36, 38 of the medical device 14 may be positioned adjacent a tissue site to be thermally-treated or ablated, where the expandable elements are in a substantially deflated, evacuated, or otherwise collapsed state. Once adequately positioned in the target region, fluid, such as a refrigerant or coolant from the console 12, may be delivered from the fluid circulation system 100 through the lumens of the shaft 26 of the medical device 14 and towards the expandable elements to inflate or otherwise expand the expandable elements within the lumen or passage defined by the blood vessel. The medical device 14 may receive coolant or refrigerant from the fluid supply 66 of the fluid circulation system 100 that bypasses the subcooling portion of the system 100 for initial positioning and expansion of the expandable elements without thermally treating the tissue.

In a particular inflation sequence, coolant may be transferred from the fluid supply 66 to the second coolant reservoir 110, and subsequently to the attached medical device 14. The coolant flowing from the fluid supply 66 to the second coolant reservoir 110 may consist of coolant vapor in a gaseous state obtained from the fluid supply 66. The coolant transfer may be achieved by having the valve 116 in a closed position, while opening valve 114, thereby placing the fluid supply 66 in fluid communication with the second coolant reservoir 110 rather than the supply line of the console 100. Once the second coolant reservoir 110 has been adequately filled with coolant to a desired level, the coolant from the second coolant reservoir 110 may then be transferred towards the exhaust lumen 106, and subsequently to the exhaust line of the coupled medical device 14. During the transfer from the fluid supply 66 to the second coolant reservoir 110, the valve 118 may be configured to prevent coolant from being transferred into the exhaust lumen until desired.

In this inflation phase, both the valve 116 and the valve 134 are closed, while valve 118 provides fluid communication between the second coolant reservoir 110 and the exhaust lumen 106 at the umbilical connector 102, and thus providing fluid communication with the exhaust lumen of the medical device 14. Since both valves 116 and 134 are closed, the medical system is configured into a closed system with the coolant from the second coolant reservoir 110. Accordingly, the volume of coolant provided to the medical device 14 from the second coolant reservoir 110 may be adjusted to provide an expected or predetermined pressure level within a portion of the medical device. In particular, as in the case with the medical device 14, the fixed volume being provided by the second coolant reservoir 110 may be selected to produce a target inflation pressure in the expandable element(s) 36, 38 of the treatment region 34. This target level may be used to insure that the expandable element(s) 36, 38 are indeed inflated to a desired degree. While a particular desired or target pressure within a portion of the medical device 14 may vary by application or specification of a particular medical device, the target pressure may be in a range of approximately atmospheric pressure to approximately 30 psia. Moreover, as the pressure within the exhaust lumen 106, and thus the expandable element(s) 36, 38 of the medical device 14, can be monitored with the pressure sensor 122, any variation in the measured pressure from the expected pressure level may indicate a leak or failure of the medical device. Moreover, as previously discussed, the second coolant reservoir 110 may have a smaller capacity than the fluid supply 66, and as such, should the medical device 14 experience a failure or leak, the amount of coolant escaping into the patient is thereby limited in amount to the capacity of the second coolant reservoir 110 rather than the fluid supply 66. This limited capacity may prevent and/or reduce the likelihood of complications arising from excess coolant entering the bloodstream, as previously suggested. In addition to verifying the structural integrity of the medical device and providing a safeguard, the inflation stage allows a physician to securely position a medical device prior to actually effecting treatment of the target tissue.

Alternative to the transfer of coolant from the fluid supply 66 to the second coolant reservoir 110 for the inflation phase, coolant may be transferred directly to the medical device from the fluid supply 66. That is, the second coolant reservoir may be removed or otherwise absent from the system, with the fluid supply 66 directing coolant for inflation of the medical device through supply lumen 104. For example, coolant flow from the coolant reservoir 108 may be allowed and modified by the valve 132, which may be adjusted or regulated to produce a target inflation pressure in a portion of the medical device, such as in the expandable element(s). This target level may be used to insure that the medical device 14 is inflated or expanded to a desired degree.

In addition, the inflation phase may include opening valve 116, and further closing 134 to place the exhaust lumen 106 in fluid communication with the controlled valve 128. As such, the medical device is placed in fluid communication with the fluid supply 66 through the supply lumen 104, and is further placed in fluid communication with the vacuum source 112 through the exhaust lumen. The inflation phase may include providing increased coolant flow within the medical device while ensuring that the medical device is appropriately expanded or inflated. This inflation may be done in the substantial absence of any cooling. For example, the subcooler 120 may be deactivated or idle during the inflation phase, such that coolant will arrive in the medical device at substantially room temperature. This may occur as no significant expansion or pressure drop may occur in the coolant supply line leading to the medical device. The absence of cooling during the inflation phase ensures that no undesirable or unwanted ablation occurs at this preliminary stage.

Subsequently, coolant may be transferred from the fluid supply 66 through the supply lumen 104 to the medical device 14 such that the coolant flow is regulated and/or controlled by the operation of the valve 132, which, as previously described, may be controlled by the second controller 130 in response to the second pressure sensor 124. In addition, the coolant flow through the medical device 14 and the exhaust line may also be affected by the operation of valve 128, which may be manipulated via a feedback loop with the first controller 126 and the first pressure sensor 122. The operation of the two controllers and the adjustable valves 132 and 128 may occur substantially simultaneously and/or alternatively in order to maintain the inflation of the expandable elements of the medical device 14 at a desired and/or target pressure as coolant flow through the medical device is increased to achieve a desired or target flow rate. For example, the valve 132 may be manipulated to provide stepped increases in flow rate and/or flow pressure from the fluid supply 66 to the supply lumen 104, where the 128 valve is adjusted in response to the setting of the valve 132 to provide adequate fluid communication with the vacuum source 112 to achieve the desired target coolant flow rate through the medical device.

Alternatively to inflating the expandable elements 36, 38 of the medical device 14 to a predetermined target pressure, the expandable elements may be inflated with a measured or metered amount of fluid in order to substantially occlude the vessel in which the expandable elements 36, 38 are positioned. For example, fluid or coolant may be delivered to the medical device 14, and during the expansion or inflation of the expandable elements, the state of occlusion of the vessel may be monitored, measured, or otherwise ascertained. Assessing the vessel occlusion may include measuring a blood or fluid pressure or flow rate in the vessel itself with one or more sensors on the medical device or through visualization modalities as known in the art. The occlusion may also be measured by measuring an impedance of tissue or fluid (or the lack thereof) of the vessel. The impedance measurement may be obtained by one or more electrodes disposed on the medical device 14 or in an auxiliary device (not shown) also positioned about the vessel.

During the delivery of coolant or fluid to the medical device 14 for the expansion of the expandable elements and the resulting occlusion of the blood vessel, the quantity (e.g., either a volume or mass) of fluid delivered to the medical device may be monitored or measured. The measurements may be taken by one or more of the sensors described herein, such as the various flow rate and/or pressure sensors distributed throughout the system 10. Because of the physical relationship between temperature, pressure, and volume for a particular substance or compound and the measurable dimensions of various portions of the system 10, it is contemplated than any of these factors may be used to calculate or determine an amount of coolant delivered to the expandable elements of the medical device during any specified time period.

The amount of fluid used to expand the expandable elements in order to sufficiently occlude a particular blood vessel or other physiological conduit can provide an indication of an inflated dimension of the expandable elements, and can further be used as a basis for selecting, modifying, or otherwise personalizing the operation of the system 10 for a given procedure on a specific patient. For example, if a particular amount of coolant is used to inflate the expandable element to achieve the desired occlusion, given a known overall volumetric capacity or other dimensional characteristics of the expandable elements, the actual amount of coolant used can be used to calculate or otherwise derive the present volumetric or dimensional state of the expandable element within the vessel. This calculated or derived dimension or size of the expendable elements (or the measured delivered coolant amount itself) can be used to select or define appropriate operating pressures, flow rates, and/or temperatures for the subsequent efficient and effective treatment of the particularly-sized expandable element and blood vessel. The measured coolant amount and resulting size of the expandable element can also be used to define a maximum operating threshold for coolant pressures or flow rates within the system 10 to reduce the likelihood of over-expansion (and potential injury to the blood vessel) or structural compromise of the medical device and the surrounding tissue in view of the measured size of the expandable elements and the blood vessel.

Once the delivered coolant amount has been measured, the size or characteristics of the expandable element and/or the blood vessel has been deduced, and target or threshold operating pressures, temperatures, and/or flow rates have been established, the fluid circulation system 100 of the console 12 may be operated in accordance with these values and settings to treat the blood vessel. For example, following the inflation phase may be a transition phase of use for the fluid circulation system 100 and/or medical device. The transition phase includes providing increased coolant flow within the medical device 14 while ensuring that the expandable element(s) 36, 38 do not deflate, which could cause the physician to lose the desired positioning or occlusion with the medical device. In particular, the transition phase may include opening valve 116, and further switching valve 118 to place the exhaust lumen 106 in fluid communication with the controlled valve 128. As such, the balloon of the catheter 1 is placed in fluid communication with the fluid supply 66 through the supply lumen 104, and is further placed in fluid communication with the vacuum source 112 through the exhaust lumen 106.

Where the inflation phase may have been provided directly from the fluid supply 66 to the medical device, the transition phase may simply consist of manipulating fluid flow via control of the valves in the supply line 104 and exhaust line 106 to reach the desired flow rate and cooling capacity similar to that of the treatment phase described below. Where the subcooler may have been inactive during the inflation phase, it may subsequently be activated to reduce the temperature of the coolant traveling along the coolant supply line 104 to again provide the desired flow rate and cooling capacity in the medical device.

Subsequently, coolant, perhaps in a liquid state, may be transferred from the fluid supply 66 through the supply lumen 104 to the expandable element(s) 36, 38 such that the coolant flow is regulated and/or controlled by the operation of the valve 132, which, as previously described, may be controlled by the second controller 130 in response to the second pressure sensor 124. In addition, the coolant flow through the expandable element(s) 36, 38 and the exhaust lumens may also be affected by the operation of valve 128, which may be manipulated via a feedback loop with the first controller 126 and the first pressure sensor 122. The operation of the two controllers and the adjustable valves 132 and 128 may occur substantially simultaneously and/or alternatively in order to maintain the inflation of the expandable element(s) 36, 38 of the medical device 14 at a desired and/or target pressure as coolant flow through the medical device is increased to achieve a desired or target flow rate. For example, the 132 valve may be manipulated to provide stepped increases in flow rate and/or flow pressure from the fluid supply 66 to the supply lumen 104 over a predetermined time period, where the 128 valve is adjusted in response to the setting of the valve 132 to provide adequate fluid communication with the vacuum source 112 to achieve the desired target coolant flow rate through the medical device.

While a suitable coolant flow rate may vary depending on the particular treatment being sought and/or depending on the dimensions and specifications of a particular medical device, the target coolant flow rate may be in the range of approximately 2,500 sccm to 15,000 sccm. The transition phase is ended when the target coolant flow rate is achieved and/or wherein further manipulation of the adjustable valves 132 and 128 is no longer desired. The transition phase may further be completed upon subjecting the supply lumen 104 and exhaust lumen 106 to an unimpeded, maximum flow rate providable by the fluid supply 66 and the vacuum source 112.

Following the transition phase and once a desired coolant flow rate has been achieved, the fluid circulation system 100 may be operated in a treatment phase. The treatment phase generally includes providing coolant flow to the medical device at the target coolant flow rate such that the desired thermal treatment may be provided to the target tissue. For example, the particular treatment may include the ablation of tissue through thermal exchange with the treatment region 34 of the medical device 14 and the surrounding tissue. The target tissue, as mentioned above, may include a blood vessel and/or innervating nerve tissue in proximity to an endoluminal passage. During the ablation or thermal exchange, one or more physiological parameters may be monitored as an indication or assessment of the efficacy of the treatment being delivered. For example, breathing and/or heart rates may be monitored as an indication of a thermal affect on nerve tissue in the vicinity of the tissue site being treated, e.g., a heart rate may change when renal nerve tissue is ablated because of the renal nerve activity and its contributing effect to heart rate and blood pressure. In similar fashion, if a portion of the phrenic nerve is subjected to thermal and/or ablative energy, it can directly affect breathing patterns, and thus the breathing rate may be monitored to assess the treatment procedure. The measuring or monitoring of the physiological parameters or patterns may be accomplished by measuring sensors or assemblies on the medical device 14 or by one or more auxiliary devices (not shown) inserted or otherwise positioned about the body.

Upon completion of the treatment phase, coolant flow to the medical device 14 may be reduced and or eliminated, but the expandable element(s) 36, 38 of the medical device may remain in an inflated state until a predetermined target temperature has been reached. In order to avoid or reduce the likelihood of unwanted tissue damage due to cryoadhesion of the device to the tissue, it may be desired to ensure that any adhesion is eliminated prior to removal and/or repositioning of the medical device. In a particular example, coolant flow from the fluid supply 66 may be reduced and/or terminated, such as by closing valve 116. In turn, valve 134 may be closed such that the adjustable valve 128 may regulate coolant evacuation from the exhaust line and thus the medical device. The valve 128 may correspondingly allow for the evacuation of coolant at a controllable rate such the expandable element (s) 36, 38 of the medical device remain in an inflated state until a predetermined target temperature is achieved at the expandable element(s) 36, 38. While applications may vary, the target temperature may be a temperature above approximately −10° C. to 20° C. to ensure that any previous ice formation is thawed, and the temperature in the expandable element(s) 36, 38 may be monitored by one or more temperature sensors affixed to the medical device in communication with the console 12. The temperature may be monitored by a temperature sensor within the expandable element(s) 36, 38, but may further be monitored by a sensor positioned on an outer surface of the expandable element(s) 36, 38 or by a sensor in thermal communication with a supply or exhaust lumen of the medical device 14. Upon achieving the predetermined target temperature, the valve 134 may then be opened, subjecting the medical device to a substantially unimpeded pressure gradient provided by the vacuum source 112, and thus allowing the balloon to collapse by the evacuation of coolant therein.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of treating tissue, comprising:
   positioning an expandable element of a medical device in a renal artery;
   delivering a fluid to the expandable element such that the expandable element is inflated to substantially occlude the renal artery;
   measuring an amount of the fluid delivered to the expandable element;
   defining at least one of a target pressure within the expandable element, target temperature of the expandable element, and target flow rate for fluid delivery to the expandable element based at least in part on the measured amount;
   regulating fluid delivery to the expandable element to attain the at least one defined target pressure, defined target temperature, or defined target flow rate;
   thermally affecting the renal artery with the expandable element; and
   monitoring a heart rate and modifying fluid delivery to the expandable element based at least in part on the heart rate.

2. The method of claim 1, further comprising correlating the measured amount to an inflated dimension of the expandable element.

3. The method of claim 1, further comprising assessing the occlusion of the renal artery.

4. The method of claim 3, wherein assessing the occlusion of the renal artery includes measuring a pressure in the renal artery.

5. The method of claim 3, wherein assessing the occlusion of the renal artery includes measuring a flow rate in the renal artery.

6. The method of claim 3, wherein assessing the occlusion of the renal artery includes measuring an impedance with the medical device.

7. The method of claim 1, wherein thermally affecting the renal artery with the expandable element includes ablating a portion of the renal artery.

8. The method of claim 1, wherein thermally affecting the renal artery with the expandable element includes ablating nerve tissue in proximity to the renal artery.

9. The method of claim 1, wherein the fluid is a cryogenic coolant.

10. The method of claim 1, further comprising:
    terminating fluid delivery to the expandable element; and
    controllably evacuating fluid from the expandable element such that the expandable element remains substantially inflated until the expandable element achieves a predetermined temperature.

11. A method of ablating tissue, comprising:
    positioning an expandable element of a catheter in a blood vessel;
    inflating the expandable element with a refrigerant to substantially occlude the blood vessel;
    measuring a volume of the refrigerant used to inflate the expandable element;
    correlating the measured volume to an inflated dimension of the expandable element;
    defining at least one of a target pressure within the expandable element and a target flow rate for refrigerant delivery to the expandable element based at least in part on the inflated dimension;
    regulating refrigerant delivery to the expandable element to attain the at least one defined target pressure within the expandable element or defined target flow rate for fluid delivery to the expandable element;
    ablating at least a portion of the blood vessel with the expandable element; and
    monitoring a heart rate and terminating refrigerant delivery to the expandable element based at least in part on the heart rate.

12. The method of claim 11, further comprising measuring the occlusion of the blood vessel.

13. The method of claim 11, wherein the blood vessel is a renal artery.

14. The method of claim 11, further comprising:
    controllably evacuating refrigerant from the expandable element such that the expandable element remains substantially inflated until the expandable element achieves a predetermined temperature.

15. The method of claim 11, further comprising measuring a pressure within the expandable element, and modifying refrigerant delivery based at least in part on the measured pressure.

16. The method of claim 11, further comprising measuring a flow rate of refrigerant being delivered to the expandable element, and modifying refrigerant delivery based at least in part on the measured flow rate.

17. A method of ablating tissue, comprising:
    positioning an expandable element of a catheter in a blood vessel;

inflating the expandable element with a volume of refrigerant to substantially occlude the blood vessel;
measuring the volume of refrigerant used to inflate the expandable element;
monitoring a heart rate;
correlating the measured volume to an inflated dimension of the expandable element;
defining at least one of a target pressure within the expandable element and a target flow rate for refrigerant delivery to the expandable element based at least in part on the inflated dimension;
measuring at least one of a pressure within the expandable element and a flow rate of refrigerant being delivered to the expandable element;
regulating refrigerant delivery to the expandable element based at least in part on the measured pressure or measured flow rate to attain the at least one defined target pressure or defined target flow rate;
ablating at least a portion of the blood vessel with the expandable element; and
terminating refrigerant delivery to the expandable element based at least in part on the heart rate.

* * * * *